(12) United States Patent
Kobler et al.

(10) Patent No.: US 7,815,950 B2
(45) Date of Patent: Oct. 19, 2010

(54) KETOMETHIONINE KETALS AND DERIVATIVES THEREOF

(75) Inventors: Christoph Kobler, Alzenau (DE); Martin Hateley, Aschaffenburg (DE); Philipp Roth, Hanau (DE); Barbara Jaeger, Mainhausen (DE); Rainer Peter, Krombach (DE); Christoph Weckbecker, Gruendau-Lieblos (DE); Klaus Huthmacher, Gelnhausen (DE)

(73) Assignee: Evonik Degussa GmbH, Essen (DE)

( * ) Notice: Subject to any disclaimer, the term of this patent is extended or adjusted under 35 U.S.C. 154(b) by 427 days.

(21) Appl. No.: 11/943,082

(22) Filed: Nov. 20, 2007

(65) Prior Publication Data

US 2008/0124426 A1 May 29, 2008

(30) Foreign Application Priority Data

Nov. 24, 2006 (DE) .................. 10 2006 055 470

(51) Int. Cl.
*A23K 1/18* (2006.01)
*A23L 1/30* (2006.01)
*C07C 53/00* (2006.01)
*C07D 319/00* (2006.01)
*C07D 311/02* (2006.01)
*C07D 319/06* (2006.01)

(52) U.S. Cl. .......................... 426/2; 426/648; 562/512; 549/274; 549/283; 549/375

(58) Field of Classification Search .................. 426/2, 426/648; 562/512; 549/274, 283, 375
See application file for complete search history.

(56) References Cited

U.S. PATENT DOCUMENTS

2005/0187293 A1  8/2005  Robert et al.

FOREIGN PATENT DOCUMENTS

EP          0 400 499 A2    12/1990
WO     WO 2006/072711 A1    7/2006

OTHER PUBLICATIONS

Cooper et al. STN Document No. 82:169584, Abstract of Journal of Biological Chemistry (1975), 250(2), 527-32.*

* cited by examiner

*Primary Examiner*—D. Margaret Seaman
*Assistant Examiner*—Nizal S Chandrakumar
(74) *Attorney, Agent, or Firm*—Oblon, Spivak, McClelland, Maier & Neustadt, L.L.P.

(57) ABSTRACT

Ketomethionine ketals and hemiketals and derivatives thereof are useful as feed additives, in particular for the nutrition of ruminants.

25 Claims, No Drawings

KETOMETHIONINE KETALS AND DERIVATIVES THEREOF

BACKGROUND OF THE INVENTION

1. Field of the Invention

The present invention relates to ketomethionine ketals and hemiketals and derivatives thereof and their production and use as feed additives.

2. Description of the Background Art

Amino acids such as methionine, lysine or threonine are, as feed additives, important components of animal nutrition. They make possible more rapid growth and also more efficient feed utilization. This usually represents an important economic advantage. The markets for feed additives are of great industrial and economic importance. In addition, they are great growth markets which is due, not least, to the increasing importance of countries such as China and India, for example.

WO 2004008874 discloses, inter alia, that methionine is the first limiting amino acid for many animal species, including ruminants. For instance in the case of dairy cows, for example, efficient milk production with respect to the amount and quality is greatly dependent on a sufficient supply of methionine. The methionine requirement of high performance dairy cows cannot be covered in this case by the microbial protein formed in the rumen or by protein from the feed not degraded in the rumen (Graulet et al., *J. Animal and Feed Sciences* (2004), 269). It is therefore advantageous to supplement methionine to the feed to increase the economic efficiency of milk production and the quality of the milk.

In the case of monogastric animals such as, for example, poultry and pigs, customarily, as feed additive, use is made of methionine and the Methionine Hydroxy Analogue (MHA), which is also termed hydroxymethylthiobutyric acid (HMB). This increases the available amount of L-methionine in the body which can then be available to the animal for growth.

In contrast thereto, supplementation of the feed with methionine is ineffective in ruminants, since the majority is degraded by microbes in the rumen of ruminants. Owing to this degradation, therefore, only a fragment of the methionine supplemented passes into the small intestine of the animal, where generally the absorption of methionine into the blood proceeds.

WO 99/04647 describes the use of MHA for ruminants. Therein it is asserted that MHA is only in part broken down in the rumen and therefore at least 20-40% of the supplemented MHA, after absorption in the small intestine, can pass in to metabolism. In numerous other publications, in contrast, the mode of action of MHA in ruminants is discussed differently. For instance, WO 200028835, for example, describes that MHA can only successfully pass through the rumen and finally into the small intestine for absorption when MHA is administered in very large amounts of 60-120 g/day/animal. However this precludes economic efficiency.

In order that methionine products such as D,L-methionine or rac-MHA are available to ruminants with high efficiency, a form protected against rumen degradation must be used. The challenge in this case is to find a suitable methionine product which gives the methionine a rumen stability as high as possible and nevertheless ensures high and efficiency absorption of the methionine in the gut. There is a plurality of possibilities in this case of giving D,L-methionine or rac-MHA these properties:

a) Physical protection:

By application of a suitable protective layer or distribution of the methionine in a protective matrix, a high rumen stability can be achieved. As a result, the methionine can pass through the rumen virtually without loss. In its further course, the protective layer is then, for example, opened or removed by acid hydrolysis in the abomasum and the methionine released can then be absorbed by the animal in the small intestine. The protective layer or protective matrix can consist of a combination of a plurality of substances such as, for example, lipids, inorganic materials and carbohydrates. The following product forms are commercially available:

i) MET-PLUS™ from Nisso America is a lipid-protected methionine having a D,L-methionine content of 65%. The protective matrix consists of the calcium salts of long chain fatty acids such as, for example, lauric acid. As preservative, butylated hydroxytoluene is used.

ii) MEPRON® M85 from Degussa AG is a carbohydrate-protected methionine which has a core of D,L-methionine, starch and stearic acid. As protective layer, ethylcellulose is used. The product has a content of 85% D,L-methionine.

iii) SMARTAMINE™ M from Adisseo is a polymer-protected methionine. The pellets, in addition to stearic acid, contain at least 70% D,L-methionine. The protective layer contains vinylpyridine-styrene copolymer.

Although the physical protection prevents microbial breakdown of methionine in the rumen and as a result the supply and utilization of methionine in the animal can be increased, there are some serious disadvantages.

The production or coating of methionine is usually a technically complicated and laborious process and is therefore expensive. In addition the surface coating of the finished pellets can easily be damaged by mechanical load and abrasion during feed processing which can lead to reduction or up to complete loss of the protection. Therefore, it is also not possible to process and repellet the protected methionine pellets to form a larger compound feed pellet, since, as a result, again the protecting layer would break owing to the mechanical stress. This greatly restricts the use of such products, since compound feed pelleting is a widely used method of feed processing.

b) Chemical protection:

Increased rumen stability of methionine can, in addition to purely physical protective possibilities, also be achieved by modifying the chemical structure, for example by esterifying the carboxylic acid group. Currently, the following products are commercially available or are described in the literature:

i) Methionine esters such as, for example, D,L-tert-butyl-methionine: The esters have been tested and demonstrated only moderate rumen stability (Loerch and Oke; "Rumen Protected Amino Acids in Ruminant Nutrition" in "Absorption and Utilization of Amino Acids" Vol. 3, 1989, 187-200, CRC Press, Boca Raton, Fla.). For D,L-tert-butylmethionine, in contrast, in WO 0028835, a biological value of 80% was published.

ii) METASMART™ from Adisseo is the racemic isopropyl ester of MHA (HMBi). This compound is also marketed under the trademark "Sequent" by the American company Novus. In WO 00/28835, a biological value of at least 50% for HMBi in ruminants was published. In this case, especially, the surprisingly rapid absorption of the hydrophobic HMBi through the rumen wall plays a decisive role. The ester can then be hydrolysed to MHA in the blood and, after oxidation and subsequent transamination, can be converted to L-methionine. In the patent EP 1358805, a comparable biological value for HMBi was published. In these studies, HMBi was applied to a porous support. In a further publication, the European Commission reported that, again, approximately 50% HMBi is absorbed via the rumen wall (European Commission: Report of the Scientific Committee on Animal Nutrition on the Use of HMBI; 25 Apr. 2003). Graulet et al. published in 2004 in the Journal of Animal and Feed Science (269), that better diffusion through the rumen wall is enabled by the lipophilic properties of the isopropyl group of HMBi.

For the production of HMBi, two different processes have been published. Thus, HMBi can either be synthesized directly in one stage from the corresponding cyanohydrin (WO 00-59877). Esterification to give the isopropyl ester proceeds in this case in situ, without needing to isolate MHA in advance. Another process, in contrast, esterifies pure MHA with isopropanol (WO 01-58864 and WO 01-56980). In both cases, for the synthesis, use is made of prussic acid which is expensive and in addition is a great potential hazard.

iii) Ketomethionine and its carboxylic acid derivatives: The use of this class of compounds, in particular of ketomethionine itself, as feed additives was first described recently in application WO 2006-072711. There, a technical process for producing ketomethionine and carboxylic acid derivatives thereof was also described. Ketomethionine is the direct precursor of methionine and can readily be converted in the body to L-methionine in one step by means of transamination. In comparison therewith, both MHA and HMBi have the disadvantage that they require two or three steps for conversion to L-methionine in the body. For instance, HMBi must first be hydrolysed to free MHA and subsequently oxidized to ketomethionine with the aid of an oxidase. Not until then can in turn the ketomethionine be directly reductively aminated to give L-methionine [Baker; "Utilization of Precursors for L-Amino Acids" in "Amino Acids in Farm Animal Nutrition" (D'Mello, J. P. F., ed.), 1994, 37-64. CAB Intl., Wallingford, Oxon, UK].

Free ketomethionine as α-ketocarboxylic acid and its salts such as, for example, the sodium or calcium salt, are compounds already known from the literature for a long time and have been produced both biochemically and chemically. Meister, for example, obtained the sodium salt of α-ketomethionine in a yield of 77% by the L-amino oxidase-catalysed oxidation of methionine (Meister, *J. Biol. Chem.* 1952, 197, 309). Previously, Waelsch et al., showed that the amino oxidases present in liver can convert methionine to α-ketomethionine (Waelsch et al., J. Am. Chem. Soc. 1938, 61, 2252). Mosbach et al., likewise described the production of ketomethionine by the L-amino oxidase-catalysed oxidation of methionine. In this case immobilized Providencia sp. PCM 1298 cells were used (Mosbach et al., Enzyme Microb. Technol. 1982, 4, 409).

As a further possible synthesis method, Sakurai et al. in 1957 published the first chemical synthesis route for synthesising α-ketomethionine. In this case, as key step, methyl-α-methoxalyl-γ-methylmercaptopropionate was hydrolyzed with dilute hydrochloric acid to give ketomethionine (Sakurai et al., *J. of Biochemistry* 1957, 44, 9, 557). Yamada et al. published virtually simultaneously the same synthesis route, after first attempts at synthesizing α-ketomethionine via an α-oximo ester formed as an intermediate gave only low yields. (Chibata et al., *Bull. Agr. Chem. Soc. Japan* 1957, 21, 6, 336).

The biological value of the sodium salt of α-ketomethionine was determined for the first time in 1977 in feeding experiments with rodents and poultry and is significantly above that of MHA (Baker and Harter, Proceedings for the Society for Experimental Biology and Medicine 1977, 156, 2001). In ruminants, α-ketomethionine and salts thereof, however, are broken down in the rumen and therefore offer no advantages over HMBi or methionine. As free α-ketocarboxylic acid, α-ketomethionine in addition has the further disadvantage that it dimerizes in a very short time and subsequently irreversibly cyclizes and therefore is not stable as a monomer of biological value and therefore is avoided in direct use as feed additive.

SUMMARY OF THE INVENTION

Against the background of the disadvantages of the background art, it is an object of the present invention to provide a rumen-stable, chemically protected methionine product for ruminants, in particular for dairy cows, which can serve as efficient methionine source for the animals and which does not have the disadvantages of the known products, or has them to a decreased extent. This would have the advantage that milk production and quality could be thereby increased, which would lead to a significant increase in economic efficiency.

A further object is to provide a feed and a feed additive of very high biological value which should have good handleability and storability and also stability under the customary conditions of compound feed processing, in particular pelleting. The product, in addition, should be useable in animal nutrition in the most general possible way as feed additive. This and other objects have been achieved by the present invention the first embodiment of which includes a chemical compound of the general formula I

wherein A is selected from the group consisting of formulae (1), (2), (3), (4) and (5),
wherein formula (1) is

wherein R=OH, OM, OR', $NH_2$, NHR' or NR'R",
wherein $R^1$, $R^2$, R' and R" are identical or different and are in each case a branched or straight-chain $C_1$-$C_{18}$-alkyl or $C_3$-$C_{18}$-cycloalkyl, allyl, benzyl, phenyl or $C_1$-$C_{18}$ alkyloxymethyl, $C_2$-$C_6$-hydroxyalkyl, $C_3$-$C_6$-dihydroxyalkyl, or a $C_3$-$C_{12}$ sugar radical in which one OH group of the sugar is replaced in each case by the ketal-O atom, by the carboxylic acid-O atom or by the carboxamide-N atom, and
wherein M is an alkali metal ion or alkaline earth metal ion or a monovalent or divalent transition metal ion;
wherein formula (2) is

wherein R=OH, OM, OR', $NH_2$, NHR' or NR'R",
wherein R' and R" are identical or different and are in each case a branched or straight-chain $C_1$-$C_{18}$-alkyl or $C_3$-$C_{18}$- cycloalkyl, allyl, benzyl, phenyl or $C_1$-$C_{18}$-alkyloxymethyl, $C_2$-$C_6$-hydroxyalkyl, $C_3$-$C_6$-dihydroxyalkyl, or a $C_3$-$C_{12}$ sugar radical in which one OH group of the sugar is replaced by the carboxylic acid-O atom or by the carboxamide-N atom, wherein M is an alkali metal ion or alkaline earth metal ion or a monovalent or divalent transition metal ion, and wherein $R^3$ is a $C_2$-$C_4$-alkylene bridge or a $C_3$-$C_{12}$ sugar radical in which two OH groups of the sugar are replaced by the two ketal-O atoms;

wherein formula (3) is

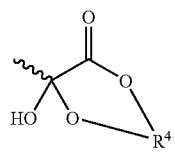

(3)

wherein $R^4$ is a $C_3$-$C_6$-alkylene radical which, optionally, is hydroxy substituted, or a $C_3$-$C_{12}$ sugar radical in which one OH group of the sugar is replaced by the ketal-O atom and one is replaced by the carboxylic acid-O atom;

wherein formula (4) is

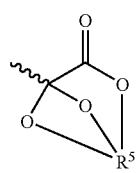

(4)

wherein $R^5$ is a $C_3$-$C_6$-alkylene radical which, optionally, is hydroxy substituted, or a $C_3$-$C_{12}$ sugar radical in which three OH groups of the sugar are replaced by both ketal-O atoms and by the carboxylic acid-O atom;

wherein formula (5) is

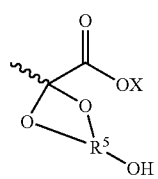

(5)

wherein $R^5$ is a $C_3$-$C_6$-alkylene radical which, optionally, is hydroxy substituted, or a $C_3$-$C_{12}$ sugar radical in which two OH groups of the sugar are replaced by the two ketal-O atoms, and wherein X=H or M.

The present invention also relates to a method of producing a feed, comprising:

adding the above compound to a feed.

The present invention also relates to a feed preparation, comprising at least one compound as above.

The present invention also relates to a process for producing carboxylic acid or ester compound of the general formula I, comprising:

reacting ketomethionine with a corresponding monovalent, divalent, trivalent alcohol or a $C_3$-$C_{12}$ sugar in the presence of an acid catalyst to give an ester product of the formulae I,1 or 2, wherein R=OR', or to give an ester product I,3 or 4, or to give an acid product I,1 or 2, wherein R=OH, or to give an acid product I,5, wherein X=H;

wherein, in the case of formulae I,1 and I,2 the radical R is not OM, $NH_2$, NHR' or NR'R".

The present invention also relates to a process for producing a carboxylic acid or a carboxylic acid salt of the general formulae I, 1 or 2 or 5 as above, comprising:

reacting an ester product of the formulae I, 1 or 2 wherein R=OR', or of the formula 4 by saponification with an alkali metal hydroxide or alkaline earth metal hydroxide or a monovalent or divalent transition metal hydroxide into the corresponding carboxylic acid salt of the formulae I,1 or 2 wherein R=OM or of the formula I,5 where X=M and optionally a free carboxylic acid wherein R=OH or X=H is liberated therefrom using a mineral acid;

wherein the radical R=OH or OM and the radical X=H or M.

The present invention also relates to a process for producing a carboxylic acid salt of the general formulae I, 1 or 2 or I,5 as above, comprising:

neutralizing an acid product of the formulae I, 1 or 2, wherein R=OH or an acid product of the formula I, 5 wherein X=H with an alkali metal or alkaline earth metal or a monovalent or divalent transition metal hydroxide or carbonate to give the corresponding carboxylic acid;

wherein the radical R=OM and the radical X=M.

In another embodiment, the present invention also relates to a process for producing ester compounds of the general formulae I, 1 or 2 as above, wherein R=OR', comprising:

reacting an ester product I, 1 or 2, by transesterification with alkali metal alkoxide M'OR" to obtain a corresponding ester product of the formulae I,1 or 2, with the proviso that R' in the ester product I, 1 or 2 used must not be equal to the radical R' in the alkoxide M'OR' used.

DETAILED DESCRIPTION OF THE INVENTION

The above object and also other objects not explicitly mentioned, but which can readily be derived or deduced from the contexts discussed herein are achieved by the ketomethionine ketals of the invention and derivatives thereof according to formula I, in particular use thereof as feed, preferably for ruminants. Thereby, not only the disadvantages of the "physically protected" methionine variants, such as, for example, Smartamine, but also the disadvantages of the "chemically protected" variants, such as, for example, HMBi, are overcome.

The present invention relates to a chemical compound of the general formula I

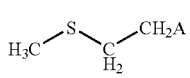

(I)

wherein A=

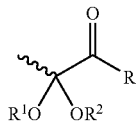

(1)

and R=OH, OM, OR', NH₂, NHR' or NR'R", wherein R¹, R², R' and R" are identical or different and are in each case a branched or straight-chain $C_1$-$C_{18}$-alkyl or $C_3$-$C_{18}$-cycloalkyl, allyl, benzyl, phenyl or $C_1$-$C_{18}$-alkyloxymethyl, preferably $C_2H_5OCH_2$ $C_2$-$C_6$-hydroxyalkyl, preferably $HOC_2H_4$—, $C_3$-$C_6$-dihydroxyalkyl, preferably $(HO)_2C_3H_5$—, or a $C_3$-$C_{12}$ sugar radical in which one OH group of the sugar is replaced in each case by the ketal-O atom, by the carboxylic acid-O atom or by the carboxamide-N atom and M is an alkali metal ion or alkaline earth metal ion, preferably $Na^+$, $K^+$, $Mg^{2+}$ or $Ca^{2+}$ or a monovalent or divalent transition metal ion, preferably $Zn^{2+}$, $Mn^{2+}$, $Cu^{2+}$ or $Cr^{2+}$, or A=

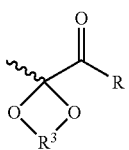

(2)

and R=OH, OM, OR', NH₂, NHR' or NR'R", wherein R' and R" are identical or different and are in each case a branched or straight-chain $C_1$-$C_{18}$-alkyl or $C_3$-$C_{18}$-cycloalkyl, allyl, benzyl, phenyl or $C_1$-$C_{18}$-alkyloxymethyl, preferably $C_2H_5OCH_2$ $C_2$-$C_6$-hydroxyalkyl, preferably $HOC_2H_4$—, $C_3$-$C_6$-dihydroxyalkyl, preferably $(HO)_2C_3H_5$—, or a $C_3$-$C_{12}$ sugar radical in which one OH group of the sugar is replaced by the carboxylic acid-O atom or by the carboxamide-N atom and M is an alkali metal ion or alkaline earth metal ion, preferably $Na^+$, $K^+$, $Mg^{2+}$ or $Ca^{2+}$ or a monovalent or divalent transition metal ion, preferably $Zn^{2+}$, $Mn^{2+}$, $Cu^{2+}$ or $Cr^{2+}$, and R³ is a $C_2$-$C_4$-alkylene bridge, preferably $C_2H_4$, or a $C_3$-$C_{12}$ sugar radical in which two OH groups of the sugar are replaced by the two ketal-O atoms, or A=

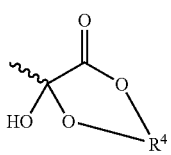

(3)

and R⁴ is a $C_3$-$C_6$-alkylene radical which, if appropriate, is hydroxy substituted, preferably —$CH_2$—$C(CH_3)_2$—$CH_2$— and —$CH_2$—$C(CH_2OH)_2$—$CH_2$—, or a $C_3$-$C_{12}$ sugar radical in which one OH group of the sugar is replaced by the ketal-O atom and one is replaced by the carboxylic acid-O atom, or A=

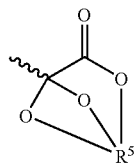

(4)

and R⁵ is a $C_3$-$C_6$-alkylene radical which, if appropriate, is hydroxy substituted, preferably —$CH_2$—CH(—)—$CH_2$—, or a $C_3$-$C_{12}$ sugar radical in which three OH groups of the sugar are replaced by both ketal-O atoms and by the carboxylic acid-O atom, or A=

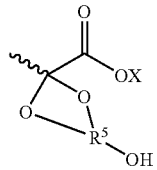

(5)

and R⁵ is a $C_3$-$C_6$-alkylene radical which, if appropriate, is hydroxy substituted, preferably —$CH_2$—CH(—)—$CH_2$—, or a $C_3$-$C_{12}$ sugar radical in which two OH groups of the sugar are replaced by the two ketal-O atoms, and wherein X=H or M and M has the meaning given above.

Preference in this case is given to a compound of the formula I,2, in which R=hydroxyl and R³=$C_2H_4$:

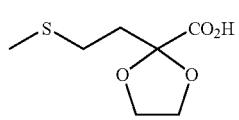

This can readily be produced by ketalization of ketomethionine with stoichiometric amounts of ethylene glycol in the presence of acid catalysts or with superstoichiometric amounts of ethylene glycol and subsequent saponification of the ketomethionine ethylene ketal ethylene glycol ester formed as an intermediate with alkali and subsequent neutralization (cf. Example 2).

Further preference is given to a compound according to formula I,2, in which R=OR' and R'=$C_1$-$C_{18}$-alkyloxy and R³=$C_2H_4$. This compound can be produced by esterification of ketomethionine with a corresponding $C_1$-$C_{18}$-alcohol in the presence of acid catalysts, and preferably subsequent ketalization with ethylene glycol.

Particular preference is given in this case to a compound according to formula I,2, in which R'=$C_1$-$C_4$-alkyloxy.

Further preference is given to a compound according to formula I,2, in which R=OR' and R'=hydroxyethoxy and R³=$C_2H_4$:

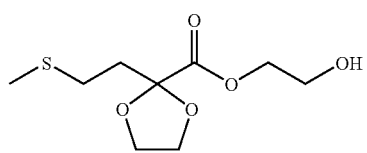

Still more preference is given to a compound according to formula I,3, in which $R^4$ is a $C_5H_{10}$ radical or a $C_5H_{10}O_2$ radical.

Particular preference is given in this case to a compound characterized by the formula

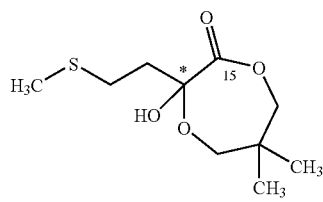

which can be produced from ketomethionine and neopentylidene glycol in the presence of acid catalysts.

Likewise preference is given to an analogous compound of the formula

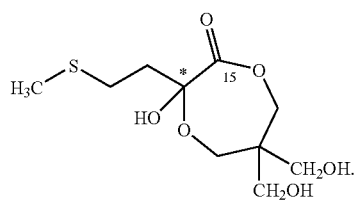

which can be produced from ketomethionine and pentaerythritol in the presence of acid catalysts.

Further preference is given to a compound according to formula I,4, in which $R^5$ is a $C_3H_5$ radical.

Particular preference is given in this case to a compound characterized by the formula (1,2-ketal)

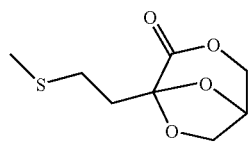

or the isomeric formula (1,3-ketal)

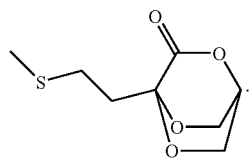

Both compounds, the 1,2-ketal and the 1,3-ketal, can be produced from ketomethionine and glycerol in the presence of acid catalysts, preferably under dehydrating conditions.

All compounds of the general formula I are outstandingly suitable according to the invention for use in animal nutrition, preferably for nutrition of farm animals.

Preference is given in this case to use for nutrition of ruminants, in particular dairy cows.

For this purpose, the compounds of the invention can be used for producing feeds.

In this case, again preference is given to use for producing feeds for ruminants.

Likewise, the present invention relates to feed preparations containing at least one of the abovementioned compounds of the invention, preferably for nutrition of ruminants.

Accordingly, mixtures of the compounds of the invention with conventional feeds can be produced.

For this, the compounds of the invention are mixed in suitable amounts into commercially conventional feed types, such as mineral feed, organic feed (for example soybean meal) or dairy compound feed.

Suitable amounts are generally proportions of 0.1% to 5% of methionine equivalents in the form of the compounds of the invention, wherein the proportions are different depending on the type of feed. Dairy compound feed is preferably mixed with <0.5% methionine equivalents, mineral feed with up to 5% and organic feed in the range from 0.5 to 3%, preferably up to 1%. One methionine equivalent in this context is the part by weight of compound of the invention which is equivalent to the same amount of methionine on a molar basis.

The present invention further relates to a process for producing carboxylic acid or ester compounds of the general formula I, 1-5, wherein, in the case of formula I,1 and 2 the radical is not OM, $NH_2$, NHR' or NR'R", characterized in that ketomethionine is reacted with a corresponding monovalent, divalent, trivalent alcohol or a $C_3$-$C_{12}$ sugar in the presence of acid catalysts to give the ester product of the formulae 1-2, where R=OR', or to give the ester product 3-4 or to give the acid product 1-2, where R=OH, or to give the acid product 5 where X=H.

Corresponding to said preferred compounds, in this case one process is preferred in which, as alcohol, use is made of a branched or straight-chain $C_1$-$C_{18}$-alkyl alcohol or $C_3$-$C_{18}$-cycloalkyl alcohol, allyl alcohol, benzyl alcohol, phenyl alcohol, $C_2$-$C_6$-hydroxyalkyl alcohol, preferably $HOC_2H_4OH$, $C_3$-$C_6$-dihydroxyalkyl alcohol, preferably glycerol or a $C_3$-$C_{12}$ sugar, preferably glyceraldehyde, dihydroxyacetone, glucose, fructose or sucrose.

In this case, in particular by suitable selection of the amount of mole equivalents of the alcohol or sugar required for the ketalization, the formation of the desired product can be influenced. When one mol equivalent of $C_1$-$C_{18}$-alkyl alcohol is used, the corresponding ester not according to the invention is preferentially formed, when two mol equivalents are used, the carboxylic acid ketal of the formula I,1 where R=OH is preferentially formed and when three mol equivalents are used, the corresponding ester ketals of the formula I,1 where R=OR' are preferentially formed. Correspondingly, when one half mol equivalent of $C_2$-$C_6$-hydroxyalkyl alcohol is used, (such as, for example, $HOC_2H_4OH$) correspondingly two hydroxy equivalents of the corresponding carboxylic acid ketal of the formula I,2 where R=OH and $R^3$=$C_2H_4$ are formed.

The production of carboxylic acid or ester compounds can advantageously be carried out in the presence of a solvent. Suitable solvents are, for example, aromatic hydrocarbons such as benzene or toluene, and also chlorinated hydrocarbons, such as methylene chloride or chloroform, and alcohols.

In the interest of a yield as high as possible of desired condensation products, in this case preference is given to a process in which water formed during the reaction is removed from the equilibrium. This can be achieved both by distillation, preferably by using a solvent and/or entrainer such as, for example, toluene. It is advantageous in this case when the solvent simultaneously acts as entrainer and, if appropriate, further as reactant. Also, in this case, the alcohols used for esterification or ketalization can additionally be used as solvent and/or entrainer.

When used as entrainer, the solvent should have a suitable boiling point. This should generally not exceed 120° C. Alcohols suitable for this purpose are, for example, $C_1$-$C_4$-alkyl alcohols, that is to say methanol, ethanol, 1- or 2-propanol and 1- or 2-butanol, isobutanol, tert-butanol.

A further possibility for removing water is the use of dehydrating agents, for example orthoesters, such as, for example trimethyl or triethyl orthoacetate. The methyl or ethyl acetate formed as coupling products can subsequently readily be removed from the reaction mixture by distillation and reused.

In this case the carboxylic acids or carboxylic acid salts of the general formula I,1-2 or 5, in which the radical R=OH or OM and the radical X=H or M, can preferably be produced by converting a carboxylic ester product of the formula I,1 or 2 where R=OR', or of the formula I,4, into the corresponding carboxylic acid salt of the formula I,1 or 2 where R=OM or of the formula 5 where X=M by saponification with an alkali metal hydroxide or alkaline earth metal hydroxide or a monovalent or divalent transition metal hydroxide and, if appropriate, liberating therefrom the free carboxylic acid where R=OH or X=H with the aid of a mineral acid. Suitable mineral acids in this case are, in particular, sulphuric acid, hydrochloric acid and phosphoric acid.

The invention also relates to a process for producing carboxylic acid salts of the general formula I,1-2 or 5, wherein the radical R=OM or the radical X=M, which is characterized in that an acid product of the formula I,1-2 where R=OH or an acid product of the formula I,5 where X=H is neutralized with an alkali metal or alkaline earth metal or a monovalent or divalent transition metal hydroxide or carbonate to give the corresponding carboxylic acid.

For production of the abovementioned carboxylic acid salts by saponification or neutralization, in this case, as hydroxides, use is preferably made of NaOH, KOH, Mg$(OH)_2$, Ca$(OH)_2$, Zn$(OH)_2$ or Mn$(OH)_2$ and, as carbonates, $Na_2CO_3$, $K_2CO_3$, $MgCO_3$, $CaCO_3$, $ZnCO_3$ or $MnCO_3$.

The invention also relates to a process for producing carboxamides of the general formula I,1-2 where R=$NH_2$, NHR', NR'R", characterized in that an ester product of the formula I,1-2, where R=OR', is converted into the corresponding amide by reaction with a nitrogenous base of the formula $NH_3$, $NH_2R'$ or NHR'R".

The invention also relates to a process for producing ester compounds of the general formula I,1-2, where R=OR', which is characterized in that an ester product I, 1-2, is converted into a corresponding ester product of the formula I, 1-2 by transesterification with an alkali metal alkoxide M'OR' (M'=alkali), with the proviso that R' in the ester product I, 1-2 used must not be equal to the radical R' in the alkoxide M'OR' used. Ketomethionine ketal esters once produced can in this manner be very readily converted into other desired ketomethionine ketal esters.

The ketomethionine ketals of the general formula I,1,2 or 5 where R=OH or OM respectively, X=H or M are polar and non-lipophilic compounds. Owing to the ketal protecting group, these compounds are rumen-stable and cannot be microbially degraded. As a result of the lipophobic carboxylic acid group, however, they are not absorbed via the rumen wall as with HMBi, but pass without breakdown into the abomasums of the ruminant, where they are hydrolysed owing to the strongly acidic conditions. The ketomethionine released is then subsequently absorbed in the small intestine.

The ketomethionine ketal esters of the general formula I,1,2 where R=OR', or of the general formula I,4 are lipophilic and non-polar compounds. Owing to the two chemical protecting groups "ketal" and "ester", these compounds are rumen-stable. The absorption, in contrast to ketomethionine ketals, proceeds rapidly and effectively via the rumen wall similarly to the mechanism of HMBi. The subsequent enzymatic cleavage to give the free ketomethionine then proceeds in the blood of the ruminant.

The use of ketomethionine ketals or ketomethionine ketal esters thus makes possible for the first time an active control of the absorption site of the "methionine equivalent".

The ketomethionine ketals or ketomethionine ketal esters and derivatives thereof have a plurality of advantages over the compounds known in the background art:

In contrast to free ketomethionine, ketomethionine ketals, ketomethionine ketal esters, ketomethionine hemiketal esters and ketomethionine ketal amides of the general formula I are chemically stable with respect to dimerization and cyclization, a precondition for storage and transport as feed additives.

Use of the compounds of the general formula I permits the active control of the absorption site in the body of the ruminant. In this case the hydrophilic ketomethionine ketals of the formula I,1,2 where R=OH, OM, or of the formula I,5 where X=H, M are absorbed in the small intestine after hydrolysis in the abomasum, and the absorption of the lipophilic ketomethionine ketal esters of the general formula I,1,2 where R=OR', or of the general formula I,4 proceeds directly via the rumen wall.

In the case of use of certain diols such as, for example ethylene glycol, or selected triols such as, for example, glycerol, or sugars such as, for example, glucose, as building blocks for ketal or ester formation with ketomethionine to give the corresponding compounds of the general formula I, these additionally have a nutritive action, owing to the sugar or alcohol building blocks which can be released again in the body.

Ketomethionine ketals and ketomethionine ketal esters have a very high biological value, since they can be hydrolysed in vivo to give α-ketomethionine. The biological value of ketomethionine in this case is significantly higher than that of MHA, since, in contrast thereto, it can be converted to L-methionine in the body in only one stage. In contrast, MHA requires two stages and HMBi even three stages.

The high biological value of ketomethionine ketals and ketomethionine ketal esters is a significant economic advantage, since less feed additive is required.

On account of the chemical protection, the product and with it the rumen protection can not be damaged by physical forces such as, for example, friction. Therefore, in comparison with a physically protected methionine form, such as, for example Smartamine, it is possible to pellet ketomethionine ketals, ketomethionine ketal esters, ketomethionine hemiketal esters and ketomethionine ketal amides of the general formula I. This is an extraordinary advantage, because a broad usability in compound feed production and final processing is thereby ensured.

In addition, the said compounds of the general formula I can generally be used as feed additives in farm animal husbandry, that is to say also in the nutrition of poultry or pigs.

In particular, ketomethionine ketals and ketomethionine ketal esters can be produced in a simpler manner, and thus generally at lower production costs, than physically protected methionine forms.

The symmetrical ketomethionine ketals of the general formula I are achiral in contrast to MHA, HMBi or D,L-methionine. Natural L-methionine is formed directly from these achiral precursors in the animal body. Conversion of the unnatural enantiomer is omitted thereby. The examples hereinafter show possibilities for producing the compounds according to the invention without acting in a limiting manner in this case.

Having generally described this invention, a further understanding can be obtained by reference to certain specific examples which are provided herein for purposes of illustration only, and are not intended to be limiting unless otherwise specified.

EXAMPLES

Example 1

Release of ketomethionine from its salts (not according to the invention)

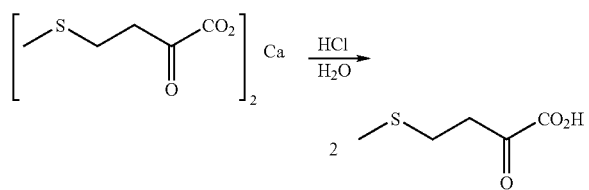

To a suspension of 43.3 g of calcium ketomethioninate (M=334.42 g/mol, 98% purity, 21% water content in the dry mass) in 120 ml of $H_2O$ and 320 ml of diethyl ether, a 10% strength aqueous hydrochloric acid solution was added slowly dropwise at 0° C. with vigorous stirring until the pH was <2. After phase separation, the aqueous phase was washed three times, each with 120 ml of diethyl ether. Subsequently, the combined organic phases were dried over $Na_2SO_4$. After filtration of the desiccant, the diethyl ether was distilled off on a rotary evaporator at 30° C. and slight vacuum. The last solvent residues were removed in high vacuum. There remained 29.1 g of a slightly yellowish oil of free ketomethionine (yield=98%, M=148.18 g/mol).

$^1$H-NMR of calcium ketomethioninate 500 MHz, DMSO-d6):

δ=2.04 (s, 3H, $CH_3$), 2.62 (t, $^3J$=7.3 Hz, 2H, $CH_2$), 2.82 (t, $^3J$=7.3 Hz, 2H, $CH_2$).

$^1$H-NMR of ketomethionine (500 MHz, DMSO-d6):

δ=2.06 (s, 3H, $CH_3$), 2.66 (t, $^3J$=7.2 Hz, 2H, $CH_2$), 3.09 (t, $^3J$=7.2 Hz, 2H, $CH_2$).

$^{13}$C-NMR of ketomethionine (125.8 MHz, DMSO-d6): δ=14.7 ($CH_3$), 26.7 ($CH_2$), 38.5 ($CH_2$), 162.2 (COOH), 194.9 (CO).

Example 2

Production of ketomethionine ketals of the formula I,2 exemplified by the reaction of ketomethionine and ethylene glycol

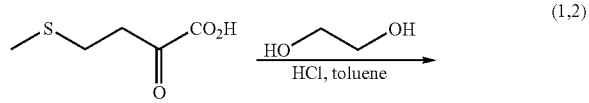

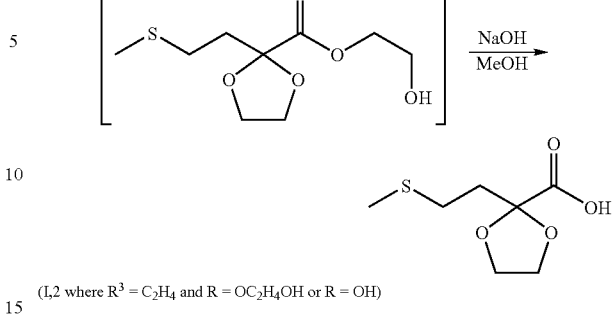

(I,2 where $R^3$ = $C_2H_4$ and R = $OC_2H_4OH$ or R = OH)

A solution of ketomethionine (174 mmol, M=148.18 g/mol) in toluene (100 ml) was added dropwise over the course of 2 h to a solution of 1 g (~3 mol %) p-toluenesulphonic acid as catalyst and ethylene glycol (335 mmol, M 62.07 g/mol) in toluene (250 ml) and the reaction was kept under reflux until no more water separated off at the attached water separator (approximately 2 h). Subsequently the toluene was taken off under vacuum and the crude product was admixed with methanol (200 ml) and, after addition of an aqueous solution of 2M sodium hydroxide (200 ml) saponified under alkaline conditions for approximately 2 h. The reaction solution was subsequently extracted by shaking with diethyl ether and the aqueous phase was acidified with dilute hydrochloric acid. The product was extracted at pH 1-2 with diethyl ether, the organic phase washed with water, dried over $Na_2SO_4$ and the solvent removed on a rotary evaporator. The oily product (I,2) was subsequently recrystallized from methylene chloride/n-hexane and was obtained as white crystalline solid. (24.6 g, yield=74%, M=192.23 g/mol, melting point: 74° C. methylene chloride/n-hexane).

$^1$H-NMR of 2-(2-(methylthio)ethyl)-1,3-dioxolane-2-carboxylic acid (I,2) (500 MHz, $CDCl_3$): δ=2.11 (s, 3H, $SCH_3$), 2.24-2.28 (m, 2H, $CH_2$), 2.58-2.61 (m, 2H, $CH_2$), 4.07-4.14 (m, 4H, $OCH_2CH_2O$).

$^{13}$C-NMR of 2-(2-(methylthio)ethyl)-1,3-dioxolane-2-carboxylic acid (I,2) (125.8 MHz, $CDCl_3$): δ=15.5 ($SCH_3$), 27.1 ($CH_2$), 34.9 ($CH_2$), 66.1 (2 $OCH_2$), 105.9 (C), 174.1 (COO).

Elemental analysis for $C_7H_{12}O_4S$ (M=192.24 g/mol): C, 43.74; H, 6.29; S, 16.68. found: C, 43.80; H, 6.25; S, 16.61.

Example 3

Production of the calcium salt of ketomethionine ketal by neutralization

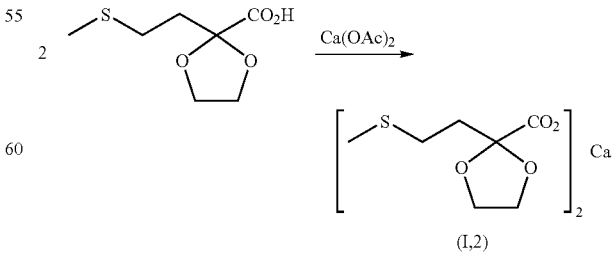

To a solution of 1.0 g (5.20 mmol) of 4-(methylthio)-2-ketobutyric acid ethylene ketal in 2.0 ml of water and 3.0 ml of acetone was added slowly dropwise at RT an aqueous solution of 0.44 g of calcium acetate (93% strength) in 2 ml of water. Subsequently 3 ml of acetone were added and the mixture was stirred overnight at RT. The white solid formed was filtered off by suction and washed thoroughly with 100 ml of a 1:10 water/acetone mixture. The product was subsequently dried in a drying cabinet and in high vacuum. (0.96 g, yield=82%, 6.3% water content by K.F. method).

$^1$H-NMR of calcium 2-(2-(methylthio)ethyl)-1,3-dioxolane-2-carboxylate (I,2) (500 MHz, DMSO-D6): δ=1.98-2.00 (m, 2H, CH$_2$), 2.03 (s, 3H, SCH$_3$), 2.44-2.47 (m, 2H, CH$_2$), 3.81-3.84 (m, 2H, CH$_2$), 3.95-4.00 (m, 2H, CH$_2$).

$^{13}$C-NMR of calcium 2-(2-(methylthio)ethyl)-1,3-dioxolane-2-carboxylate (I,2) (125.8 MHz, DMSO-D6/DCl): δ=15.1 (SCH$_3$), 27.0 (CH$_2$), 35.2 (CH$_2$), 65.7, 66.0 (2 OCH$_2$), 105.6 (C), 171.0 (COO).

Example 4

Production of ketomethionine hemiketal esters I,3 exemplified by the reaction of ketomethionine and 2,2-dimethyl-1,3-propanediol

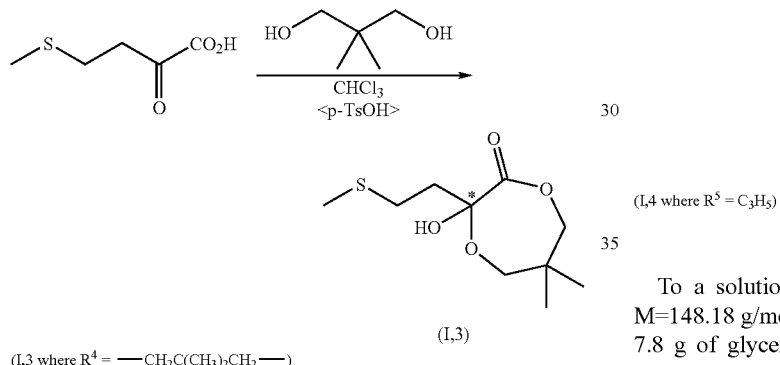

(I,3 where R$^4$ = —CH$_2$C(CH$_3$)$_2$CH$_2$—)

To a solution of 11.1 g of ketomethionine (75 mmol, M=148.18 g/mol) in 200 ml of absolute ethanol-free chloroform were added 8.9 g of 2,2-dimethyl-1,3-propanediol (85 mmol, M=104.15 g/mol) and 0.8 g (~5 mol %) of p-toluene-sulphonic acid as catalyst and the mixture was kept under reflux until water no longer separated off (approximately 3.5 h) at the attached water separator. After cooling, the solution was washed with half-saturated NaHCO$_3$ solution, the aqueous phase was further rewashed with chloroform and the combined organic phases dried over Na$_2$SO$_4$. After filtration, the solvent was removed on a rotary evaporator and the oily crude product was crystallized from methylene chloride/n-hexane. The product (I,3) was obtained as white crystalline solid (10.8 g, yield=62%, M=234.32 g/mol, melting point=109° C. (methylene chloride/n-hexane)).

$^1$H-NMR of rac-4,4-dimethyl-7-hydroxy-7-(2-(methylthio)ethyl)-6-oxacaprolactone (I,3) (500 MHz, CDCl$_3$): δ=0.92 (s, 3H, CH$_3$), 0.99 (s, 3H, CH$_3$), 2.04-2.19 (m, 2H, CH$_2$), 2.08 (s, 3H, SCH$_3$), 2.47-2.52 (m, 1H, SCHH), 2.61-2.66 (m, 1H, SCHH), 2.92 (d, $^2$J=8.0 Hz, 1H, OCHH), 3.25 (d, $^2$J=8.0 Hz, 1H, OCHH), 3.72 (d, $^2$J=10.4 Hz, 1H, COOCHH), 4.30 (d, $^2$J=10.4 Hz, 1H, COOCHH), 4.50 (s, 1H, OH).

$^{13}$C-NMR of rac-4,4-dimethyl-7-hydroxy-7-(2-(methylthio)ethyl)-6-oxacaprolactone (I,3)(125.8 MHz, CDCl$_3$): δ=15.7 (SCH$_3$), 21.9, 21.3 (2 CH$_3$), 27.7 (CH$_2$), 37.7 (CH$_2$), 66.0 (OCH$_2$), 70.9 (OCH$_2$), 96.5 (COH), 172.5 (COO).

Elemental analysis for C$_{10}$H$_{18}$O$_4$S (M=234.32 g/mol): C, 51.26; H, 7.74; S, 13.68. found: C, 50.82; H, 7.73; S, 13.52.

Example 5

Production of ketomethionine ketal esters I,4 as exemplified by the reaction of ketomethionine and glycerol

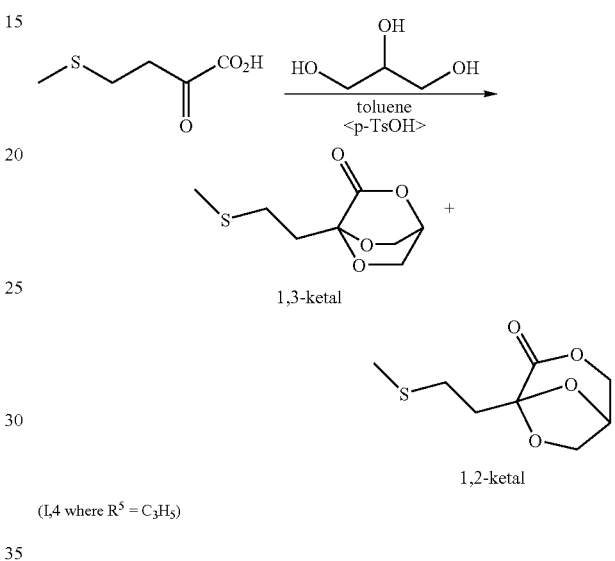

(I,4 where R$^5$ = C$_3$H$_5$)

To a solution of 12.0 g of ketomethionine (81 mmol, M=148.18 g/mol) in 120 ml of absolute toluene were added 7.8 g of glycerol (1,2,3-propanetriol)(85 mmol, M=92.09 g/mol) and 0.8 g (~5 mol %) of p-toluene-sulphonic acid as catalyst and the mixture was kept under reflux until no more water separated off (approximately 2.5 h) at the attached water separator. After cooling, the solution was washed with half-saturated NaHCO$_3$ solution, the aqueous phase was further rewashed with chloroform and the combined organic phases were dried over Na$_2$SO$_4$. After filtration, the solvent was removed on a rotary evaporator and the oily crude product (ratio (1,3-ketal: 1,2-ketal=70:30) was chromatographed (diethyl ether/n-hexane 1:1). This separated the two compounds from one another. The main product (1,3-ketal) crystallized in the form of colourless needles from a mixture of methylene chloride/n-hexane (8.8 g, yield=53%, M=204.25 g/mol, melting point=39.5° C. (methylene chloride/n-hexane)).

$^1$H-NMR of 4-(2-(methylthio)ethyl)-2,5,8-trioxabicyclo [2.2.2]octan-3-one (1,3-ketal) (500 MHz, CDCl$_3$): δ=2.13 (s, 3H, SCH$_3$), 2.17-2.20 (m, 2H, CH$_2$), 2.65-2.68 (m, 2H, CH$_2$), 4.12-4.13 (m, 4H, 2 CH$_2$), 4.76 (s, 1H, CH).

$^{13}$C-NMR of 4-(2-(methylthio)ethyl)-2,5,8-trioxabicyclo [2.2.2]octan-3-one (1,3-ketal) (125.8 MHz, CDCl$_3$): δ=15.4 (SCH$_3$), 26.9, (CH$_2$), 33.2 (CH$_2$), 66.5 (2 OCH$_2$), 70.9 (CH), 92.9 (C), 166.2 (COO).

Elemental analysis for C$_8$H$_{12}$O$_4$S (M=204.25 g/mol): C, 47.04; H, 5.92; S, 15.70. found: C, 47.21; H, 5.93; S, 15.69.

Example 6

Production of ketomethionine ketal salts of the formula I,5 as exemplified by saponification of 1,2-ketal or 1,3-ketal from Example 5

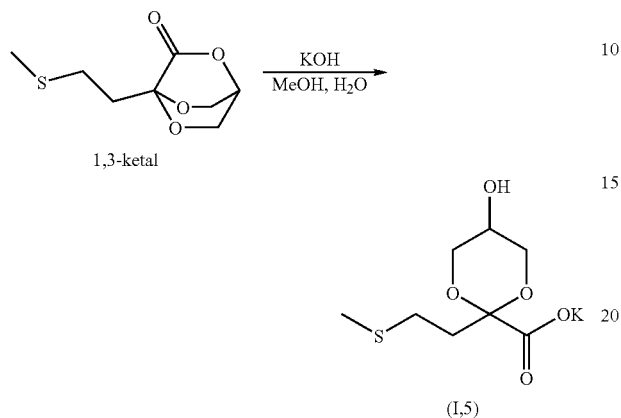

To a suspension of 50 mg (0.24 mmol) of the 1,3-ketal from Example 5 in 1.0 ml of methanol and 1.5 ml of water were added 15 mg of potassium hydroxide at room temperature and the solution was stirred for 30 min at room temperature. After removal of the solvent and drying under vacuum, the product was obtained as a white solid. (0.60 g, yield=96%).

$^1$H-NMR of potassium 5-hydroxy-2-(2-(methylthio)ethyl)-1,3-dioxane-2-carboxylate (500 MHz, D$_2$O/TSP): δ=1.96-2.02 (m 2H, CH$_2$), 2.10 (t, 3H, CH$_3$), 2.51-2.54 (m, 2H, CH$_2$), 3.48-3.52 (m, 2H, CH$_2$), 3.81-3.87 (m, 1H, CH), 3.98-4.01 (m, 2H, CH$_2$).

German patent application 10 2006 055470.1 filed Nov. 24, 2006, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A chemical compound of the general formula I

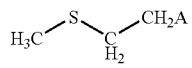

wherein A is selected from the group consisting of formulae (1), (2), (3), (4) and (5),
wherein formula (1) is

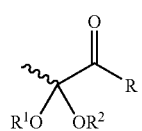

wherein R=OH, OM, OR', NH$_2$, NHR' or NR'R",
wherein R$^1$, R$^2$, R' and R" are identical or different and are in each case a branched or straight-chain C$_1$-C$_{18}$-alkyl or C$_3$-C$_{18}$-cycloalkyl, allyl, benzyl, phenyl or C$_1$-C$_{18}$ alkyloxymethyl, C$_2$-C$_6$-hydroxyalkyl, C$_3$-C$_6$-dihydroxyalkyl, or a C$_3$-C$_{12}$ sugar radical in which one OH group of the sugar is replaced in each case by the ketal-O atom, by the carboxylic acid-O atom or by the carboxamide-N atom, and wherein M is an alkali metal ion or alkaline earth metal ion or a monovalent or divalent transition metal ion;

wherein formula (2) is

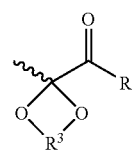

wherein R=OH, OM, OR', NH$_2$, NHR' or NR'R",
wherein R' and R" are identical or different and are in each case a branched or straight-chain C$_1$-C$_{18}$-alkyl or C$_3$-C$_{18}$-cycloalkyl, allyl, benzyl, phenyl or C$_1$-C$_{18}$-alkyloxymethyl, C$_2$-C$_6$-hydroxyalkyl, C$_3$-C$_6$-dihydroxyalkyl, or a C$_3$-C$_{12}$ sugar radical in which one OH group of the sugar is replaced by the carboxylic acid-O atom or by the carboxamide-N atom, wherein M is an alkali metal ion or alkaline earth metal ion or a monovalent or divalent transition metal ion, and wherein R$^3$ is a C$_2$-C$_4$-alkylene bridge or a C$_3$-C$_{12}$ sugar radical in which two OH groups of the sugar are replaced by the two ketal-O atoms;

wherein formula (3) is

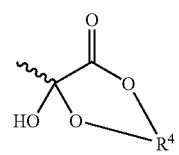

wherein R$^4$ is a C$_3$-C$_6$-alkylene radical which, optionally, is hydroxy substituted, or a C$_3$-C$_{12}$ sugar radical in which one OH group of the sugar is replaced by the ketal-O atom and one is replaced by the carboxylic acid-O atom;

wherein formula (4) is

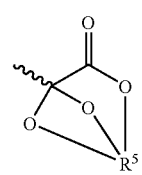

wherein R$^5$ is a C$_3$-C$_6$-alkylene radical which, optionally, is hydroxy substituted, or a C$_3$-C$_{12}$ sugar radical in which three OH groups of the sugar are replaced by both ketal-O atoms and by the carboxylic acid-O atom;

wherein formula (5) is

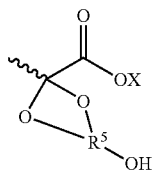

(5)

wherein $R^5$ is a $C_3$-$C_6$-alkylene radical which, optionally, is hydroxy substituted, or a $C_3$-$C_{12}$ sugar radical in which two OH groups of the sugar are replaced by the two ketal-O atoms, and wherein X=H or M.

2. The compound according to claim 1, wherein R=hydroxyl and $R^3$=$C_2H_4$.

3. The compound according to claim 1, wherein R=OR' and R'=$C_1$-$C_{18}$-alkyloxy and $R^3$=$C_2H_4$.

4. The compound according to claim 3, wherein R'=$C_1$-$C_4$-alkyloxy.

5. The compound according to claim 1, wherein R=OR' and R'=hydroxyethoxy and $R^3$=$C_2H_4$.

6. The compound according to claim 1, wherein $R^4$ is a $C_5H_{10}$ radical or a $C_5H_{10}O_2$ radical.

7. The compound according to claim 6, having the formula:

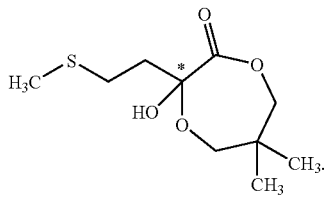

8. The compound according to claim 6, having the formula:

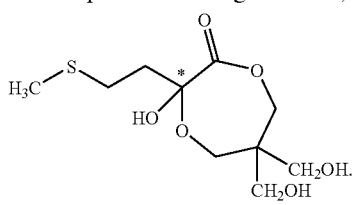

9. The compound according to claim 1, wherein $R^5$ is a $C_3H_5$ radical.

10. The compound according to claim 9, having the formula:

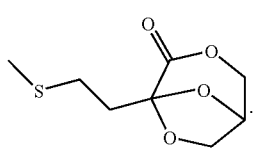

11. The compound according to claim 9, having the formula:

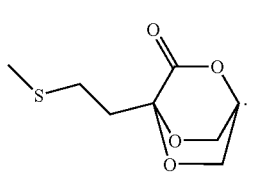

12. An animal nutritional composition, comprising: the compound according to claim 1.

13. The composition of claim 12, wherein said animal is a ruminant.

14. A method of producing a feed, comprising:
adding the compound according to claim 1 to a feed.

15. A method of feeding a ruminant, comprising:
providing a feed produced according to claim 14 to a ruminant.

16. A feed preparation, comprising at least one compound according to claim 1.

17. A process for producing a carboxylic acid or ester compound of the general formula I according to claim 1, comprising:
reacting ketomethionine with a corresponding monovalent, divalent, trivalent alcohol or a $C_3$-$C_{12}$ sugar in the presence of an acid catalyst to give an ester product of the formulae I,1 or 2, wherein R=OR', or to give an ester product I,3 or 4, or to give an acid product I,1 or 2, wherein R=OH, or to give an acid product I,5, wherein X=H;
wherein, in the case of formulae I,1 and I,2 the radical R is not OM, $NH_2$, NHR' or NR'R".

18. The process according to claim 17, wherein said alcohol is used and wherein said alcohol is selected from the group consisting of a branched or straight-chain $C_1$-$C_{18}$-alkyl alcohol or $C_3$-$C_{18}$-cyclo-alkyl alcohol, allyl alcohol, benzyl alcohol, phenyl alcohol, $C_2$-$C_6$-hydroxyalkyl alcohol, $C_3$-$C_6$-dihydroxyalkyl alcohol, a $C_3$-$C_{12}$ sugar and mixtures thereof.

19. The process according to claim 17, wherein water formed during the reaction is removed.

20. A process for producing a carboxylic acid or a carboxylic acid salt of the general formulae I, 1 or 2 or 5 according to claim 1, comprising:
reacting an ester product of the formulae I, 1 or 2 wherein R=OR', or of the formula 4 by saponification with an alkali metal hydroxide or alkaline earth metal hydroxide or a monovalent or divalent transition metal hydroxide into the corresponding carboxylic acid salt of the formulae I,1 or 2 wherein R=OM or of the formula I,5 where X=M and optionally a free carboxylic acid wherein R=OH or X=H is liberated therefrom using a mineral acid;
wherein the radical R=OH or OM and the radical X=H or M.

21. A process for producing a carboxylic acid salt of the general formulae I, 1 or 2 or I,5 according to claim 1, comprising:
neutralizing an acid product of the formulae I, 1 or 2, wherein R=OH or an acid product of the formula I, 5 wherein X=H with an alkali metal or alkaline earth metal or a monovalent or divalent transition metal hydroxide or carbonate to give the corresponding carboxylic acid;
wherein the radical R=OM and the radical X=M.

22. The process according to claims 20 or 21, wherein said hydroxide is NaOH, KOH, $Mg(OH)_2$, $Ca(OH)_2$, $Zn(OH)_2$ or $Mn(OH)_2$.

23. The process according to claims 20 or 21, wherein said carbonate is $Na_2CO_3$, $K_2CO_3$, $MgCO_3$, $CaCO_3$, $ZnCO_3$ or $MnCO_3$.

24. A process for producing carboxamides of the general formulae I,1 or 2 according to claim 1, comprising:
reacting an ester product of the formula I,1 or 2, wherein R=OR', with $NH_3$, $NH_2R'$ or NHR'R" to obtain the corresponding amide;
wherein R=$NH_2$, NHR', NR'R".

25. A process for producing ester compounds of the general formulae I, 1 or 2 according to claim 1, wherein R=OR', comprising:
reacting an ester product I,1 or 2, by transesterification with alkali metal alkoxide M'OR' to obtain a corresponding ester product of the formulae I, 1 or 2, with the proviso that R' in the ester product I, 1 or 2 used must not be equal to the radical R' in the alkoxide M'OR' used.

* * * * *